(12) United States Patent
van de Wardt et al.

(10) Patent No.: US 11,383,099 B2
(45) Date of Patent: Jul. 12, 2022

(54) WIRELESS AFTERLOADER

(71) Applicant: NUCLETRON OPERATIONS B.V., Veenendaal (NL)

(72) Inventors: Cor van de Wardt, Veenendaal (NL); Johan Henning, Veenendaal (NL)

(73) Assignee: Nucletron Operations B.V., Veenendaal (NL)

(*) Notice: Subject to any disclaimer, the term of this patent is extended or adjusted under 35 U.S.C. 154(b) by 677 days.

(21) Appl. No.: 16/223,592

(22) Filed: Dec. 18, 2018

(65) Prior Publication Data

US 2020/0188690 A1 Jun. 18, 2020

(51) Int. Cl.
| | |
|---|---|
| *A61N 5/10* | (2006.01) |
| *G16H 40/67* | (2018.01) |
| *A61B 17/00* | (2006.01) |
| *A61B 18/00* | (2006.01) |

(52) U.S. Cl.
CPC .......... *A61N 5/1007* (2013.01); *G16H 40/67* (2018.01); *A61B 2017/00199* (2013.01); *A61B 2017/00212* (2013.01); *A61B 2017/00221* (2013.01); *A61B 2017/00734* (2013.01); *A61B 2018/00684* (2013.01); *A61N 2005/1008* (2013.01)

(58) Field of Classification Search
CPC .......... A61N 5/1007; A61N 2005/1008; A61N 5/1001–1029; A61N 2005/1003–1025; H04W 88/08–10; H03K 19/17728; A61B 2018/00684; B60W 2050/0026; B60T 2270/311; G05B 23/0278; G05B 2219/00–50401; G16H 40/67
See application file for complete search history.

(56) References Cited

U.S. PATENT DOCUMENTS

| | | | | |
|---|---|---|---|---|
| 2003/0001615 | A1* | 1/2003 | Sueyoshi | H03K 19/17748 326/41 |
| 2005/0086481 | A1* | 4/2005 | Winget | H04W 12/10 713/176 |
| 2015/0326037 | A1* | 11/2015 | Borhan | B60L 58/16 320/162 |
| 2016/0364981 | A1* | 12/2016 | Towers | B60Q 9/00 |
| 2017/0224290 | A1* | 8/2017 | Ishioka | A61B 5/7405 |

FOREIGN PATENT DOCUMENTS

| | | | | |
|---|---|---|---|---|
| EP | 1348464 | A1 * | 10/2003 | A61N 5/1007 |
| WO | WO-0218013 | A1 * | 3/2002 | A61N 5/1007 |
| WO | WO-2012154762 | A1 * | 11/2012 | A61N 5/1001 |

* cited by examiner

*Primary Examiner* — Catherine B Kuhlman
(74) *Attorney, Agent, or Firm* — Bookoff McAndrews, PLLC (57) ABSTRACT

Embodiments of the disclosure may be drawn to wireless afterloaders. Exemplary afterloaders may include a central processing unit, a first complex programmable logic device having a memory, a transceiver operably connected to the complex programmable logic device, wherein the transceiver is configured to wirelessly receive data from a second complex programmable logic device separate from the wireless afterloader, and a battery.

20 Claims, 4 Drawing Sheets

FIG. 4

WIRELESS AFTERLOADER

TECHNICAL FIELD

The present disclosure relates generally to brachytherapy treatment systems, and more particularly, to wireless afterloader systems.

INTRODUCTION

Afterloaders are used during brachytherapy treatment to position one or more radioactive sources inside of, or next to, an area of a subject requiring treatment, e.g., a tumor. One or more applicators, needles, and/or catheters may be positioned relative to a subject, and then an afterloader may be connected to the applicator (or other device) and used to introduce one or more radioactive sources (e.g., encapsulated radioactive isotopes or radioactive seeds) into the applicator, and thus into or next to the treatment area. Remote afterloading systems allow a healthcare provider to remotely control delivery of the radioactive sources from the afterloader and to the subject without exposing the healthcare provider to radiation. Before and after administration of radiotherapy, the radioactive source(s) may be stored within a shielded portion of the afterloader, called a safe. Transfer tubes, guide tubes, cables, or other devices may be used to move the radioactive sources from within the afterloader to predetermined positions within the applicator, in accordance with a treatment plan.

Conventional afterloader systems are wired. They may have connectors for use with a power cord to power and/or charge the afterloader, one or more signal cables to transmit information to and from the afterloader for control of the afterloader, and a potential equalization cable. Yet the wires associated with traditional afterloaders may create several issues. For example, cables in wired systems can become tangled or may extend in different directions, making it difficult to move the afterloader, thus potentially posing a safety hazard to physicians and patients. Further, cables of different lengths may be needed to accommodate the different arrangements and/or sizes of different treatment rooms, thus it may not be easy to use the same afterloader in multiple different treatment rooms and additional setup time and overhead costs may be needed. Cables and/or connectors may wear down and break, which may require replacement of the cable(s) and/or connectors and potentially the premature termination of a treatment, and current leakage from the wires to the patient may also occur. Further, if medical imaging, e.g., magnetic resonance imaging (MM) is used in the treatment room, then afterloader cables may need to be shielded and/or filtered, which may be costly.

Afterloaders according to the present disclosure may solve one or more of the problems set forth above and/or other problems in the art. The current scope of the disclosure, however, is defined by the attached claims and not by the ability to solve any specific problem.

SUMMARY OF THE DISCLOSURE

Embodiments of the disclosure may be drawn to wireless afterloaders. Exemplary wireless afterloaders may include a central processing unit, a first complex programmable logic device having a memory, a transceiver operably connected to the complex programmable logic device, wherein the transceiver is configured to wirelessly receive data from a second complex programmable logic device separate from the wireless afterloader, and a battery.

Various embodiments of the disclosure may include one or more of the following aspects: the battery may be a first battery, and the wireless afterloader may further comprise a second battery; the transceiver may be one of a Wi-Fi transceiver, a Li-Fi transceiver, an infrared transceiver, or an ultrasound transceiver; the wireless afterloader may further comprise a wireless interface for connecting to at least one of a computer, a smart phone, or a tablet; the memory may include a lookup table stored thereon; the battery may include at least one of a lead-crystal battery, a lithium-ion battery, an ultracapacitor, a supercapacitor, or a gold capacitor; the battery may be configured for wireless charging; or the battery may be configured for wired charging.

Embodiments of the disclosure may also be drawn to a brachytherapy treatment system. Exemplary systems may comprise a wireless afterloader comprising a central processing unit, a first complex programmable logic device having a memory, a first transceiver operably connected to the first complex programmable logic device, and a battery. The system may also include a junction box, a second complex programmable logic device having a memory, wherein the first complex programmable logic device is separate from the second complex programmable logic device. The system may further comprise an access point operably coupled to the junction box and the second complex programmable logic device, a second transceiver operably coupled to the access point, and at least one emergency stop switch operably coupled to the second complex programmable logic device.

Various embodiments of the disclosure may include one or more of the following aspects: the junction box may be located in a first room, and the wireless afterloader may be located within a second room; the first transceiver and the second receiver may be one of a Wi-Fi transceiver, a Li-Fi transceiver, an infrared transceiver, or an ultrasound transceiver; the battery may further include a first battery, and the system may further include a second battery operably coupled to the junction box; the second complex programmable logic device may be included as part of the junction box; the memory of the first complex programmable logic device may include a first lookup table stored thereon, and the memory of the second complex programmable logic device may include a second lookup table stored thereon; or the system may further comprise a docking station configured to store and/or charge the wireless afterloader.

Additionally, in some embodiments, a wireless afterloader may comprise a complex programmable logic device having a memory with a lookup table stored thereon, a transceiver operably connected to the complex programmable logic device, wherein the transceiver is configured to receive wireless data; and a battery. The transceiver may be configured to receive a first wireless signal, and, in response to receiving the first wireless signal, the complex programmable logic device may access the lookup table to determine whether a value associated with the first wireless signal corresponds to a value stored in the lookup table.

Various embodiments of the disclosure may include one or more of the following aspects: if the value associated with the first wireless signal does not correspond to the value stored in the lookup table, the wireless afterloader may be configured to stop administering brachytherapy treatment; the transceiver may be one of a Wi-Fi transceiver, a Li-Fi transceiver, an infrared transceiver, or an ultrasound transceiver; the battery may be a first battery, and the wireless afterloader may further comprise a second battery; the battery may include at least one of a lead-crystal battery, a lithium-ion battery, an ultracapacitor, a supercapacitor, or a gold capacitor; or the battery may be configured for wireless charging.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements, other than those specifically shown, are contemplated and are within the scope of the present disclosure.

There are many embodiments described and illustrated herein. The description is neither limited to any single aspect nor embodiment thereof, nor to any combinations and/or permutations of such aspects and/or embodiments. Moreover, each of the aspects of the described embodiments may be employed alone or in combination with one or more of the other aspects of the described embodiments. For the sake of brevity, certain permutations and combinations are not discussed and/or are illustrated separately herein. Notably, an embodiment or implementation described herein as "exemplary" is not to be construed as preferred or advantageous, for example, over other embodiments or implementations; rather, it is intended to reflect or indicate the embodiment(s) is/are "example" embodiment(s).

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish one element or structure from another. Moreover, the terms "a" and "an" herein do not denote a limitation of quantity, but rather denote the presence of one or more of the referenced items.

The terms cord, wire, cable, etc., are used interchangeably herein. The term "distal end," or any variation thereof, refers to the portion of a device farthest from an operator of the device during an injection operation. For example, the distal end of a guide tube of an afterloader may be the end inserted into the patient. Conversely, the term "proximal end," or any variation thereof, refers to the portion of the device closest to the operator of the device, e.g., the end of a guide tube closest to an afterloader. Further, as used herein, the terms "about," "substantially," and "approximately" generally mean+/−10% of the indicated value, unless indicated otherwise.

DETAILED DESCRIPTION

Figure 1:
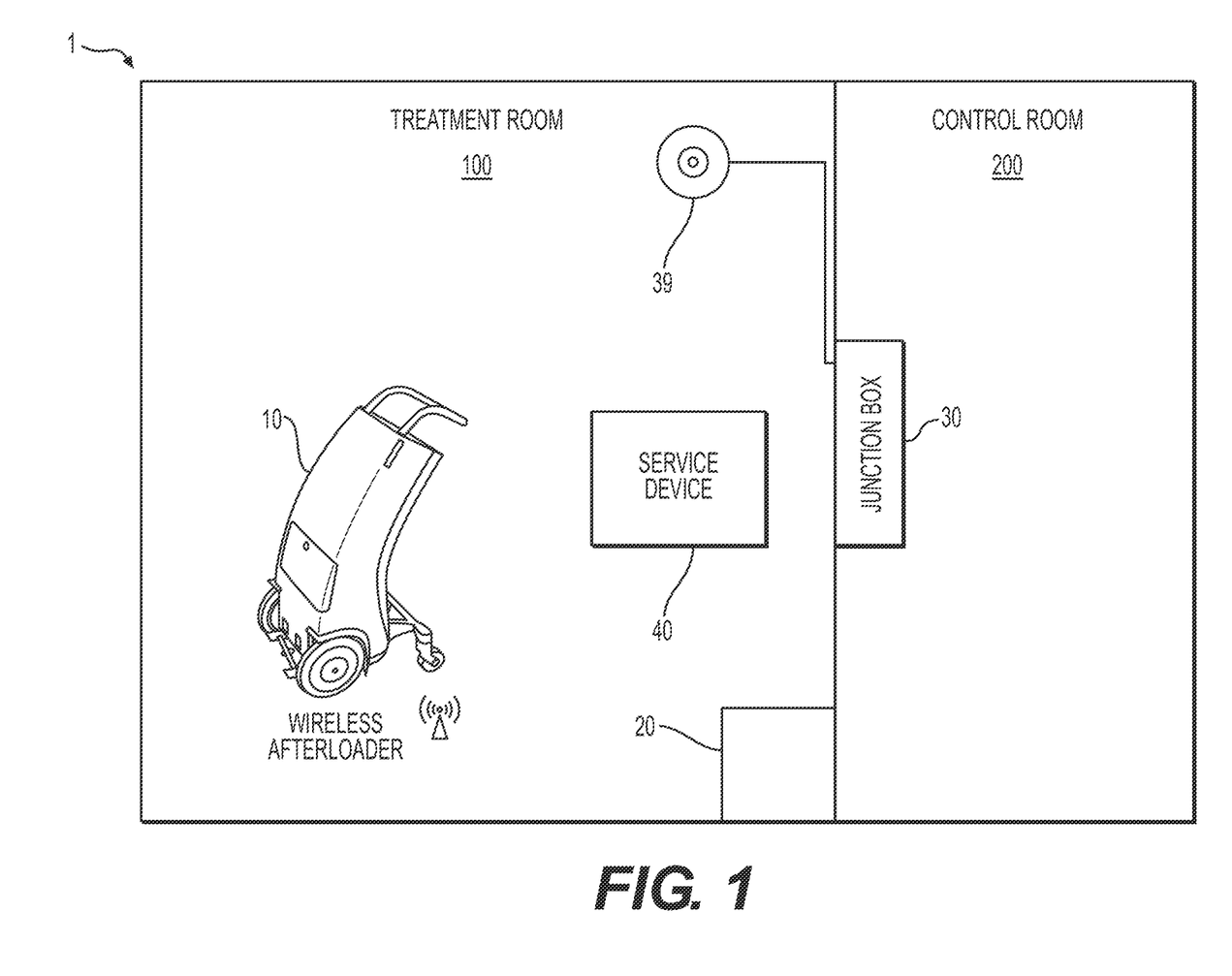
FIG. 1 depicts a schematic view of a brachytherapy treatment system, in accordance with an exemplary embodiment of the present disclosure.

FIG. 1 is an overview of an exemplary brachytherapy treatment system 1, according to an exemplary embodiment of the disclosure. Brachytherapy treatment system 1 may include a wireless afterloader 10, a junction box 30, and an access point 39. Afterloader 10 may be any suitable afterloader, e.g., a high dose rate or a pulse dose rate afterloader, and may be configured for use with various radioactive sources, e.g., iridium-192 or cobalt-60. In some embodiments, afterloader 10 may be a brachytherapy seed loader for placing one or more radioactive seeds. Access point 39 may be a Power over Ethernet (PoE) access point or any other suitable access point, depending on the type of wireless connection used, as will be described further below.

Junction box 30 may serve as the control unit and may include one or more electrical components, such as, for example, one or more of a junction box computer and/or processing system, a treatment control computer, a treatment control panel, an Ethernet switch, a PoE injector, an electromagnetically compatible filter board, or other suitable components. In some embodiments, one or more of these components may be included in junction box 30, or one or more of these components may be separate from, but operably connected to, junction box 30 via, e.g., a wired or wireless connection. A junction box computer associated with junction box 30 may act as a user interface for afterloader 10, and may have treatment server software and/or information, position server software and/or information, and/or dose rate server and/or information stored thereon. Junction box 30 may be connected to access point 39 via, e.g., an Ethernet connection, which may allow afterloader 10 to be wirelessly connected to junction box 30, allowing for wireless control of afterloader 10. Junction box 30 and/or any suitable control units included in brachytherapy treatment system 1 may be wirelessly coupled to afterloader 10 via any suitable wireless interface, e.g., Wi-Fi, Bluetooth, ZigBee, infrared, Li-Fi, or ultrasound interfaces, or any other wireless connection known to one of skill in the art.

Brachytherapy treatment system 1 may optionally include a service device 40 wirelessly coupled to one or both of afterloader 10 and junction box 30. For example, brachytherapy treatment system 1 (e.g., afterloader 10 and/or junction box 30) may include a wireless interface to allow service device 40 to connect to and communicate with the system. Service device 40 may be, for example, a computer (e.g., a desktop or laptop computer), a smart phone, a tablet, or any other suitable device. A healthcare provider may be able to control afterloader 30 using one or more service devices 40 in addition to, or instead of, junction box 30. In some embodiments, a healthcare provider or technician may be able to troubleshoot, upgrade, diagnose, and/or fix afterloader 10 using service device 40 to wirelessly access afterloader 10. In such embodiments, afterloader 10 and brachytherapy treatment system 1 may be configured to allow for remote monitoring and/or servicing via service device 40.

Brachytherapy treatment system 1 may further include a docking station 20. In some embodiments, docking station 20 may be a chest, closet, cabinet, and/or other storage unit in which afterloader 10 may be housed when not in use. In other embodiments, docking station 20 may be a region of treatment room 100 (or other room) where afterloader 10 may be kept. Afterloader 10 may operably couple to docking station 20 for recharging by a cable connection, docking station 20 may act as a docking station to charge afterloader 10 either with or without a cable connection, or docking station 20 may wirelessly charge afterloader 10. Details of docking station 20 and/or one or more batteries included in afterloader 10 will be described further below in greater detail.

The various components of brachytherapy treatment system 1—for example, afterloader 10, access point 39, service device 40, junction box 30, and/or docking station 20—may be located within a single room, such as a treatment room 100, or various elements of brachytherapy treatment system 1 may be located in separate areas. For example, some components may be located in treatment room 100, while others may be located in a control room 200 and/or other location. In some embodiments, junction box 30 may be located in control room 200, while afterloader 10 and/or access point 39 are located in treatment room 100. Docking station 20 may be located in one or more of treatment room 100, control room 200, a storage room (not shown), and/or any other suitable area.

In some embodiments, there may be multiple of the same components included as part of brachytherapy treatment system 1. For example, junction box 30 may be wirelessly connected to afterloader 10, which may be configured for use in multiple different treatment rooms. For example, multiple treatment rooms may have their own docking station 20, their own access point 39, and/or multiple different service devices 40 may be able to connect to brachytherapy treatment system 1. Afterloader 10 may be used to perform brachytherapy treatment in a first treatment room 100 and may then be moved to another treatment room to perform brachytherapy treatment in a second room. By having a docking station 20 and/or access point 39 in each of the first and second treatment rooms, there may be less setup time and/or breakdown time for use of the same afterloader 10 in different rooms. In some embodiments, junction box 30 may be configured to wirelessly control multiple different afterloaders 10 across multiple treatment rooms 100, e.g., by alternatively communicating via different access points 39 in different treatment rooms 100.

Afterloader 10 may house radioactive sources, which may be, e.g., contained within a capsule that is connected to the distal end of a cable used to maneuver the capsule. Afterloader 10 may also include one or more transfer tubes that may connect to an applicator (and/or other device) positioned within the subject. The radioactive material, capsule(s), cable(s), and/or transfer tubes may be moved or positioned relative to the afterloader 10 to cooperatively guide the radioactive material to the subject. For example, a capsule containing radioactive material may be moved using a cable from afterloader 10, through a transfer tube, and into an applicator. Various components may be configured to house and/or control movement of radioactive material, e.g., radioactive sources or seeds, to position the radioactive material relative to a subject during treatment. The radioactive material may include a radioisotope (e.g., one or more of iridium-192, cobalt-60, caesium-137, californium-252, gold-198, indium-114, palladium-103, phosphorus-32, radium-226, ruthenium-106, samarium-145, strontium-90, tantalum-182, thulium-107, tungsten-181, ytterbium-169, or iodine-125), or any other suitable radioactive material known to one of ordinary skill in the art for use in medical treatments. In some embodiments, afterloader 10 may also include one or more dummy cables and/or dummy sources (i.e., having no radioactive material) in addition to, or instead of, radioactive material. In some embodiments, afterloader 10 may include a smart dummy cable, e.g., a smart cable with electromagnetic tracking to support source position reconstruction or a smart cable for in vivo dose measurement.

Wireless afterloader 10 may be capable of delivering the radioactive material to a subject while reducing radiation exposure to medical personnel. For example, a treatment protocol for a specific subject, or for multiple subjects, may be stored on one or more of junction box 30, service device 40, a treatment control computer, a treatment control panel, and/or any other suitable components of brachytherapy treatment system 1, and treatment of the subject using afterloader 10 may be controlled wirelessly according to the treatment protocol. In some embodiments, a healthcare provider may directly control afterloader 10 to perform brachytherapy treatment wirelessly from a location outside of treatment room 100.

Figure 2:
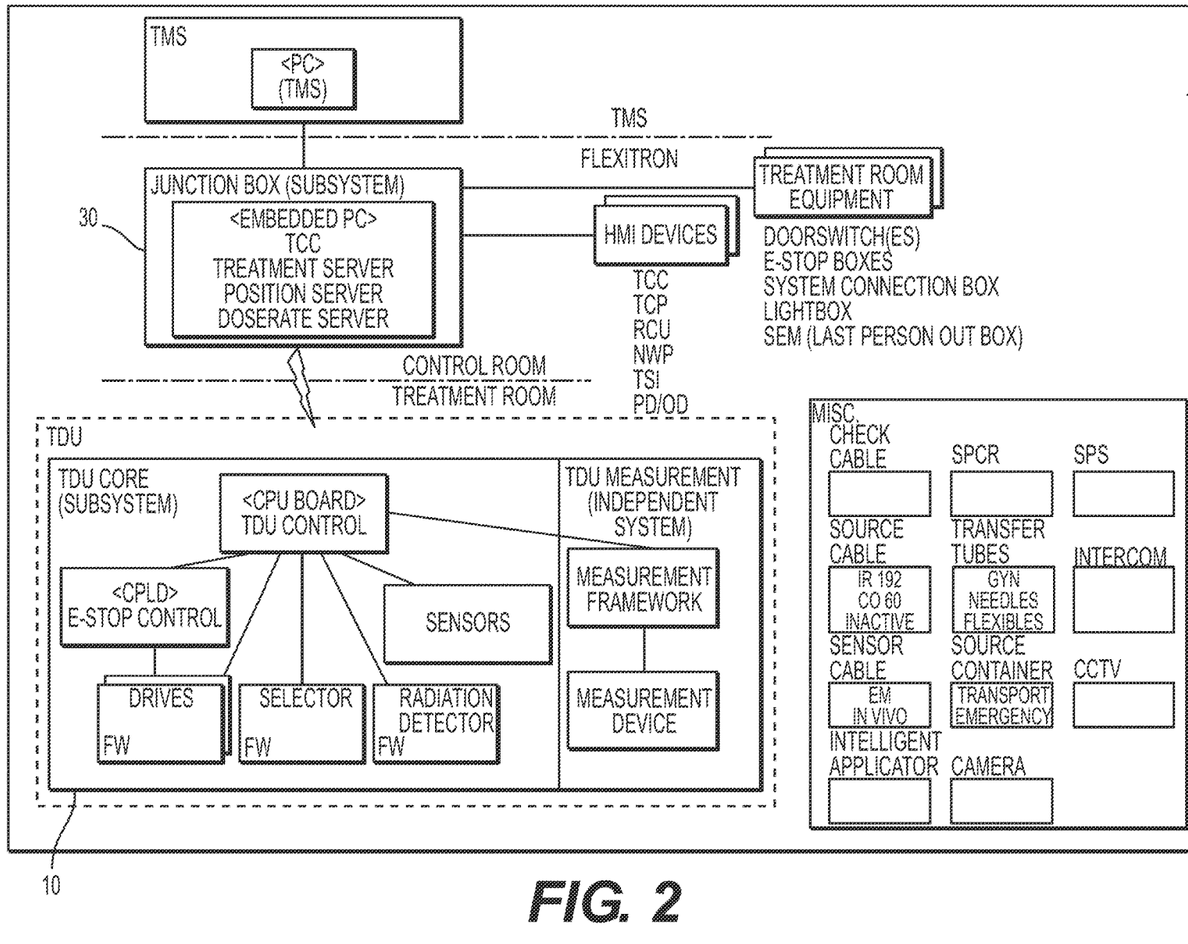
FIG. 2 depicts an architectural overview of a brachytherapy treatment system, in accordance with an exemplary embodiment of the present disclosure.

FIG. 2 depicts a variety of exemplary components that may be included in a brachytherapy system 1. The arrangement of components relative to one another is exemplary, and it is contemplated that other arrangements are possible. A treatment management system (TMS) may be operably coupled to junction box 30 located, e.g., in control room 200, either via a wired or wireless connection. Treatment information for one or more subjects may be communicated between TMS and junction box 30, which may include a treatment control computer, a treatment server, a position server, and/or a dose rate server. Junction box 30 may further be operably coupled (either via a wired or wireless connection) to one or more human machine interface (HMI) devices, which may include, e.g., one or more treatment control computers, treatment control panels, remote control units, nurse warning panels, treatment status indicators, patient displays, and/or operator displays. Junction box 30 may also be operably coupled (either via a wired or wireless connection) to treatment room equipment, e.g., one or more door switches, emergency stop (Estop) boxes, system connection boxes, light boxes, and/or start enable modules (SEMs) configured to ensure that all personnel have left treatment room 100.

As described above, junction box 30 may also be operably coupled via a wireless connection to a treatment delivery unit (TDU), e.g., an afterloader 10, which may be located in treatment room 100. Afterloader 10 may have a core including one or more of a complex programmable logic device (CPLD) (described further below), a central processing unit (CPU) board, a sensor, a drive, a selector, and/or a radiation detector. Afterloader 10 may also include, or may be operably coupled to, a TDU measurement system, which may include a measurement framework and one or more measurement devices to determine the position of radioactive material. Brachytherapy system 1 may also include components such as one or more check cables, source position check ruler (SPCR), source position simulator (SPS), source cables, transfer tubes, intercoms, sensor cables, source containers, closed-circuit television (CCTV), intelligent applicators, and/or cameras.

Figure 3:
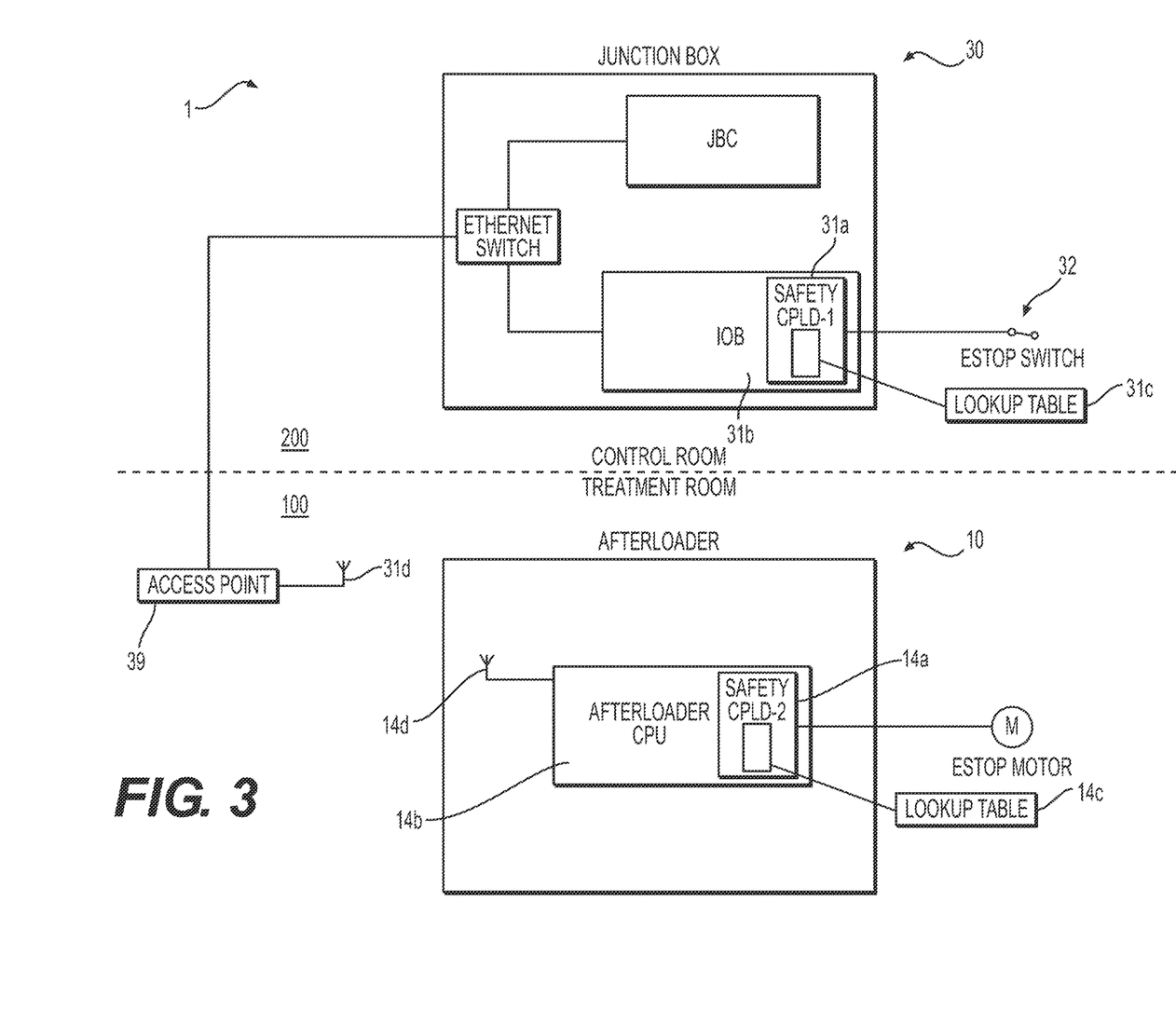
FIG. 3 depicts a schematic view of an aspect a brachytherapy treatment system, in accordance with an exemplary embodiment of the present disclosure.

With traditional, wired afterloaders, a hardwired connection may ensure that control of the wired afterloader is maintained throughout brachytherapy treatment. Cables and/or wires may be visually assessed before and/or after each treatment session to make sure there are no damaged or worn areas that may jeopardize power and/or information being sent to and from the afterloader. With wireless afterloader 10, since no hardwire connection may exist to control afterloader 10, other safety measures may be built into brachytherapy system 1. To ensure that wireless control over afterloader 10 is safely maintained and/or monitored, a safety protocol, as depicted in FIG. 3, may be used in conjunction with brachytherapy treatment system 1. The safety protocol may include two or more CPLDs configured to communicate with each other regularly throughout wireless control of afterloader 10 and/or throughout a brachytherapy treatment administered by afterloader 10. A first CPLD 14a may be incorporated into afterloader 10, e.g., as part of the afterloader CPU 14b, and a second CPLD 31a may be incorporated into junction box 30, e.g., as part of input/output board (IOB) 31b. CPLD 14a may be operably coupled to a transceiver 14d incorporated as part of afterloader 10, and CPLD 31a may be operably coupled to a transceiver 31d incorporated as part of junction box 30, access point 39, or any other suitable location. Alternatively, CPLD 14a and CPLD 31a may be operably coupled to separate transmitters and receivers as opposed to combined transceivers.

Brachytherapy treatment system 1 may also include one or more emergency stop (Estop) switches 32 operatively connected to junction box 30 either via a wired or wireless connection. Estop switch 32 may include an emergency stop button, lever, knob, switch, handle, or other suitable actuation mechanism that a person may activate in order to stop a brachytherapy treatment session being delivered, or about to be delivered, to a subject. One or more Estop switches 32 may be mounted in the control room, with junction box 30, in a hallway of a medical facility (e.g., outside of the treatment room 100 and/or outside of a control room 200), or in any other suitable location.

CPLD 14a and CPLD 31a may be in regular communication with each other via transceivers 14d and 31d so that CPLD 14a and CPLD 31a regularly confirm that they are operably connected with one another. CPLD 14a and CPLD 31a may provide a safety protocol to ensure that a control unit, e.g., junction box 30, has reliable control over afterloader 10—and thus brachytherapy treatment administered by afterloader 10—and to ensure that junction box 30 and afterloader 10 are in fact wirelessly connected.

CPLD 14a and CPLD 31a may each include a non-volatile memory on which a lookup table 14c, 31c, respectively, is stored. In operation, CPLD 31a of junction box 30 may be operably connected to one or more Estop switches 32. CPLD 31a may monitor and/or debounce the one or more Estop switches 32 regularly, e.g., approximately every 5-10 milliseconds, approximately every 5-20 milliseconds, approximately every 5-50 milliseconds, approximately every 10-20 milliseconds, approximately every 10-30 milliseconds, etc. For example, CPLD 31a may monitor and/or debounce the one or more Estop switches 32 every 10-50 milliseconds to assure that the maximum allowed overdose limit according to industry standard IEC-60601-2-17 is not reached. The IEC states that detection of an error shall happen before the subject receives an additional absorbed dose of 0.25 Gy over the intended absorbed dose at 10 mm.

In some embodiments, a wired connection may operably couple CPLD 31a with Estop switch 32, so that once Estop switch 32 is activated, a signal is automatically sent to CPLD 31a indicating that Estop switch 32 has been activated. CPLD 14a may wirelessly transmit a signal to CPLD 31a via transceiver 14d, and CPLD 31a may receive the signal from CPLD 14a via transceiver 31d. If CPLD 31a has not detected that one or more Estop switches 32 has been activated, then CPLD 31a may transmit a reply signal to CPLD 14a in response to the signal transmitted from CPLD 14a via transceiver 31d. For example, the signal from CPLD 14a may correspond to a certain value stored in lookup table 31c of CPLD 31a. CPLD 31a may access lookup table 31c in response to the signal received from CPLD 14a, may identify the value associated with the signal received from CPLD 14a, and may transmit back to CPLD 14a (via transceiver 31d) a signal that corresponds to the value associated with the signal received from CPLD 14a. CPLD 14a may receive the signal (via transceiver 14d) from CPLD 31a and may access lookup table 14c to determine whether the signal received from CPLD 31a has a value associated with it that corresponds to the value that had been associated with the signal initially sent by CPLD 14a. If the value is as anticipated, then afterloader 10 may continue operation, e.g., performing brachytherapy treatment. CPLD 14a may then generate a random number, and may transmit (via transceiver 14d) a signal indicative of that random number to CPLD 31a, starting the protocol over again. The process of sending and receiving signals between CPLD 14a and CPLD 31a may occur regularly, e.g., approximately every 5-10 milliseconds, approximately every 5-20 milliseconds, approximately every 5-50 milliseconds, approximately every 10-20 milliseconds, approximately every 10-30 milliseconds, etc. For example, signals may be sent from one CPLD to the other every 10-50 milliseconds to assure that the maximum allowed overdose limit according to industry standard IEC-60601-2-17 is not reached.

In some embodiments, instead of lookup tables, hash function, cyclic redundancy check (CRC), checksum, and/or Fletcher checksum methods may be used to uniquely identify if data is valid or not as CPLD 13a and CPLD 14a communicate with each other. In some embodiments, a sequence number may be used to confirm whether a value received from CPLD 31a or CPLD 14a is active and functioning correctly. Use of a sequence number may avoid a partially frozen system that always replies with a correct answer.

If, however, CPLD 31a detects that an Estop switch 32 has been activated, then once a signal from CPLD 14a is received, then CPLD 31a may return a signal associated with a value that is different than the value associated with the signal received from CPLD 14a in lookup table CPLD 31c. CPLD 14a may receive the different signal from CPLD 31a and may determine that the signal is different than the expected value. In response, CPLD 14a may initiate an emergency retract protocol in afterloader 10. For example, afterloader 10 may stop administering brachytherapy treatment to a subject and may retract one or more of cables, capsules, and/or radioactive material back into a shielded compartment (e.g., safe) within afterloader 10. If the main drive motor of afterloader 10 cannot perform the emergency retract protocol, then a back-up motor within afterloader 10 (which may, in some embodiments, be stronger than the main drive motor) may be activated to retract the radioactive material.

In some embodiments, medical personnel may be able to initiate an emergency retract protocol of afterloader 10 via service device 40 instead of, or in addition to, one or more Estop switches 32.

In some embodiments, if a signal from CPLD 31a to CPLD 14a is delayed or is not sent, CPLD 14a may initiate an emergency retract protocol in afterloader 10, as described above. For example, signals may be transmitted and received between CPLD 31a and CPLD 14a at regular intervals, and, if a signal is not received by CPLD 14a at the predetermined time interval, then the emergency retract protocol may be initiated in afterloader 10, ceasing brachytherapy treatment. In some embodiments, the predetermined time interval may be approximately every 5-10 milliseconds, approximately every 5-20 milliseconds, approximately every 5-50 milliseconds, 10-50 milliseconds, approximately every 10-20 milliseconds, approximately every 10-30 milliseconds, etc. In some embodiments, a threshold amount of wait time may be built in. For example, if CPLD 14a should receive a signal every 20 milliseconds from CPLD 31a, then CPLD 14a may wait slightly longer than 20 milliseconds, e.g., 21-25 milliseconds, until a threshold waiting time is met or exceeded, before triggering the emergency retract protocol in afterloader 10. In this way, CPLD 31a and CPLD 14a may communicate continuously over a wireless connection to ensure the brachytherapy treatment system 1 is operating safely and that wireless control over afterloader 10 is maintained throughout treatment. If the wireless connection between junction box 30 and afterloader 10 should fail, then brachytherapy treatment would be stopped so as to not jeopardize the subject receiving treatment.

Further, in some embodiments, a signal indicative that brachytherapy treatment has been completed may be sent between CPLD 14a and CPLD 31a to initiate removal of radioactive material. In some embodiments, an emergency-retract-like protocol may be initiated once the treatment is complete; for example, upon completion, CPLD 14a or CPLD 31a may fail to generate a signal or may generate a signal with an associated value that does not correspond to the associated value of the received signal.

Figure 4:
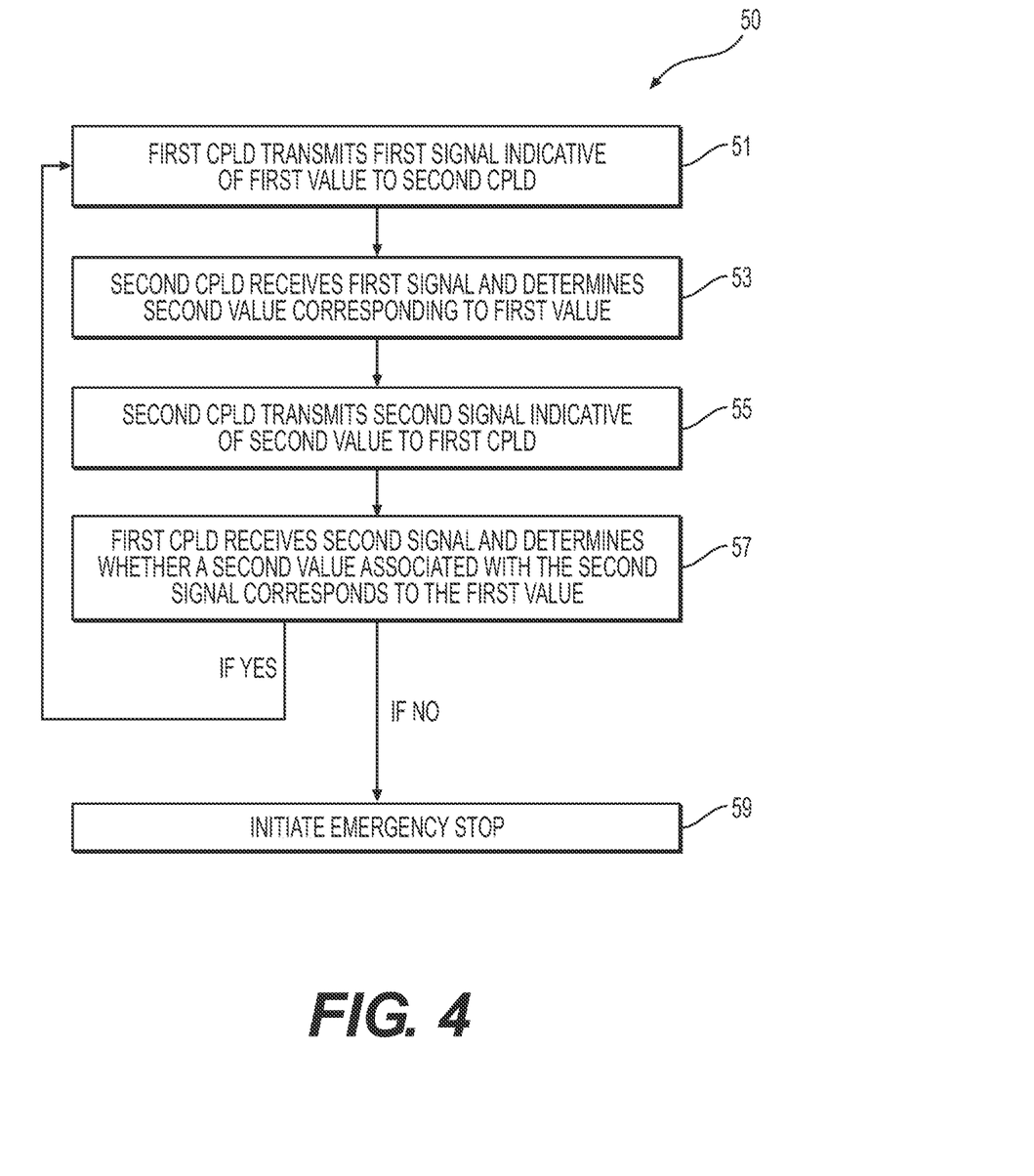
FIG. 4 is a flow chart of an exemplary brachytherapy method, according to an exemplary embodiment of the present disclosure.

FIG. 4 depicts an exemplary safety protocol method 50 executed by brachytherapy treatment system 1. CPLD 14a may transmit a signal associated with a first value from lookup table 14c to CPLD 31a (step 51). CPLD 31a may receive the first value and determine a second value corresponding to the first value using lookup table 31c (step 53). CPLD 31a may then transmit a second signal associated with the second value to CPLD 14a (step 55). CPLD 14a may compare the second value to the first value using lookup table 14c (step 57). If the second value properly corresponds to the first value in lookup table 14c, afterloader 10 may continue operating in a normal mode, and CPLD 14a may continue to send a first value to CPLD 31a (repeat step 51), continuing the cycle of receiving and transmitting signals. The cycle may be repeated until an emergency retract protocol is initiated or until the brachytherapy treatment is completed. However, if the second value does not properly correspond to the first value in lookup table 14c, afterloader 10 may begin an emergency retract protocol (step 59), described herein. In some embodiments, once brachytherapy treatment administration by afterloader 10 is complete, an inconsistent value may be sent in order to initiate the emergency retract protocol, or no signal may be received, which may also initiate an emergency retract protocol. In other embodiments, a special stop signal may be transmitted between CPLD 14a and CPLD 31a, indicating that treatment is completed and causing a stop in treatment.

In some embodiments, the first value may originate with a value stored in lookup table 31c of CPLD 31a. CPLD 31a may transmit the first value to CPLD 14a. CPLD 14a may receive the first value and determine a second value corresponding to the first value using lookup table 14c. CPLD 14a may then transmit the second value to CPLD 31a. If the second value from CPLD 14a does not correspond with the first value in lookup table 31c, CPLD 31a may transmit an emergency retract notification to CPLD 14a to initiate an emergency retract protocol of afterloader 10. Alternatively, in response to the second value not corresponding to the first value, the next first value transmitted from CPLD 31a to CPLD 14a may not correspond to any value in lookup table 14c. In this case, CPLD 14a may initiate the emergency retract protocol.

During normal operation of afterloader 10, the value associated with the signal transmitted by CPLD 14a and the value associated with the signal transmitted by CPLD 31a should correspond in respective lookup tables 14c, 31c. When an event occurs that would be considered detrimental to the brachytherapy treatment being performed by afterloader 10, one or both of these values may be changed such that the emergency retract protocol may be initiated. For example, an event that changes the value transmitted by CPLD 31a may include medical personnel actuating Estop switch 32 operably connected to CPLD 31a. If Estop switch 32 is actuated, CPLD 31a may change the value from lookup table 31c from a normal value to a value that does not have a corresponding value in lookup table 14c. Alternatively, in some embodiments, when Estop switch 32 is actuated, CPLD 31a may transmit a shutdown value to CPLD 14a. The shutdown value may be a value that initiates the emergency retract protocol of afterloader 10.

According to another exemplary embodiment, the failure of a signal to be transmitted from CPLD 31a to CPLD 14a, or vice versa, may cause the emergency retract protocol to be initiated. Thus, if CPLD 14a of afterloader 10 is not in regular contact with CPLD 31a, afterloader 10 may be configured to initiate the emergency retract protocol.

According to another exemplary embodiment, an event that may cause initiation of the emergency retract protocol may include a power dip or power failure in the treatment facility, and/or a loss of internet connection. If the power provided to CPLD 14a and/or measured by CPLD 31a falls below a certain threshold, CPLD 31a may change the value selected in lookup table 31c to a value that will cause CPLD 14a to initiate an emergency retract protocol of the afterloader 10. Alternatively, if power to CPLD 31a is lost, a value may not be transmitted to CPLD 14a, and afterloader 10 may initiate an emergency retract protocol. If internet connection is lost, then CPLD 14a and/or CPLD 31a may fail to receive signals from one another, and an emergency retract protocol of afterloader 10 may occur. As will be discussed further below, however, in some embodiments, the use of one or more batteries to power junction box 30 and/or afterloader 10 may mitigate loses of power and/or internet.

When the emergency retract protocol of afterloader 10 is initiated, afterloader 10 may abort administration of brachytherapy treatment. In the event that radioactive material is located outside of a shielded compartment of afterloader 10 during the emergency retract protocol, the radioactive material and/or any associated cables and/or capsules, may be retracted into the shielded compartment of afterloader 10. This includes retracting radioactive sources and any radioactive material from the patient, in the event the radioactive material is positioned within the patient or otherwise external to a shielded compartment of afterloader 10 at the time the emergency retract protocol is initiated.

Once the radioactive material is retracted into a shielded compartment of afterloader 10, medical personnel may disconnect the transfer tubes and/or other accessories from the patient and may move afterloader 10 away from the patient, e.g., back to a docking station 20. In some embodiments, medical personnel may move (e.g., wheel) afterloader 10 to a desired location, and in some embodiments, afterloader 10 may include motorized wheels to allow it to move about treatment room 100 or between treatment rooms 100. Once afterloader 10 is housed at docking station 20, docking station 20 may lock afterloader 10 thereto or therein.

As shown in FIG. 1, docking station 20 may be located within treatment room 100. Docking station 20 may have several features including, but not limited to a locking mechanism and/or a charging mechanism. An optional docking mechanism may include any suitable mechanism known to one of ordinary skill in the art. For example, afterloader 10 and docking station 20 may include elements that align to interlock or otherwise engage each other to retain afterloader 10 in place relative to docking station 20. In some embodiments, locking of afterloader 10 to docking station 20 may occur automatically, or a person may use a padlock, combination lock, etc., to secure components of docking station 20 and afterloader 10 to each other or to secure afterloader 10 within docking station 20. In some embodiments, the locking mechanism may include an electromagnet that may be activated remotely and/or may be activated automatically when afterloader 10 is within a certain distance of docking station 20. If docking station 20 is a cabinet, chest, closet, or other storage unit, then the storage unit may be locked either manually or automatically, once afterloader 10 is inside. Locking afterloader 10, e.g., while charging, may be desirable, because a completely wireless afterloader 10 may be easier to steal or misplace. Locking afterloader 10 may prevent movement of afterloader 10 relative to docking station 20, and thus may potentially inhibit improper charging of afterloader 10.

As described above, docking station 20 may include a suitable wired or wireless charging mechanism. For example, charging may include a contactless mechanism, such as, e.g., magnetic induction/resonance charging. In some embodiments, there may also be a fast charging option, so that if someone forgot to charge afterloader 10, quick charging may be available when afterloader 10 is needed for administering brachytherapy treatment. In some embodiments, it may be possible to charge afterloader 10 while afterloader 10 is performing brachytherapy treatment. The charging mechanism may also include a male/female connection between afterloader 10 and docking station 20, which may be achieved when afterloader 10 is docked in docking station 20. In some embodiments, afterloader 10 may be plugged into docking station 20 for charging. The locking mechanism and the charging mechanism may be any locking mechanism or charging mechanism known to those of ordinary skill in the art.

In some embodiments, afterloader 10 may include one or more batteries. For example, CPLD 14a, afterloader CPU 14b, and/or other components of afterloader 10 may receive power from a battery incorporated within afterloader 10. In some embodiments, afterloader 10 may include a main battery, as well as a secondary backup battery. The main battery may be used for normal function of afterloader 10, e.g., performing brachytherapy treatment. In the event that the main battery fails, or the charge is depleted, the secondary backup battery may take over. In some embodiments, if the main battery fails and/or loses charge during a brachytherapy treatment, then the secondary backup battery may supply power to finish the treatment. In some embodiments, however, once the secondary backup battery begins to supply power instead of the main battery, afterloader 10 may be configured to initiate an emergency retract protocol and to provide power for retracting radioactive material and/or accompanying cables and/or capsules within a compartment of afterloader 10. In other words, the secondary backup battery may be included to ensure that afterloader 10 has enough power to safely house all radioactive materials within it rather than powering administration of brachytherapy. It is also contemplated that afterloader 10 may include three batteries—e.g., a main battery, a secondary battery to finish treatment if the main battery runs out, and a third battery to provide power for performing an emergency retract protocol in the event that both the main and secondary batteries fail or are depleted. Exemplary batteries include, e.g., one or more lead-crystal, lithium-ion, ultracapacitor, supercapacitor, or gold capacitor batteries, or other suitable batteries or combinations thereof.

Embodiments of the disclosure may also incorporate intelligent monitoring solutions. For example, energy going in and out of afterloader 10 and/or junction box 30, or a component—e.g., a battery—associated therewith) may be monitored to determine how much power is being used, and/or how much battery life remains on a given battery. Battery status may be monitored before, during, and/or after treatment.

In some embodiments of the disclosure, afterloader 10 may include a replaceable battery. For example, once afterloader 10 is finished delivering treatment, someone may remove one or more batteries from afterloader 10 and replace the one or more batteries with one or more already-charged batteries. If a replaceable battery pack is incorporated, the battery pack may be recharged in afterloader 10 rather than replaced following treatment. Or, e.g., if someone forgot to charge the battery or if afterloader 10 is needed for administering another treatment, the battery may be removed and replaced with a new, charged battery.

The inclusion of one or more batteries to power afterloader 10 may mean that afterloader 10 may not require a power cord or cable to operate, making afterloader 10 truly wireless. In some embodiments, junction box 30 may also be powered by one or more batteries, in addition to, or instead of, being powered by the grid. Such embodiments may be useful, e.g., in the event that power is lost at a treatment facility. If CPLD 31a and 14a are powered by batteries incorporated in junction box 30 and afterloader 10, then treatment may continue to be administered without interruption if loss of power should occur. In addition, if access point 39 is also powered by a battery, then Wi-Fi signals may be maintained, allowing for uninterrupted treatment administration in a Wi-Fi embodiment. If, however, internet connection is lost, then Wi-Fi embodiments may not be able to administer treatment, and the emergency retract protocol may be initiated when CPLD 31a and/or CPLD 14a fail to receive a signal. It is further contemplated that afterloader 10 and/or junction box 30 may include one or more batteries, but may also be configured for use with a power cord in the event that the battery fails, is not charged, and/or if wireless connection is lost or is not desired.

As described above, wireless afterloader 10 may use any suitable wireless technology. While Wi-Fi embodiments are described herein, Wi-Fi in some treatment facilities may be unreliable, or if MRI is used during brachytherapy treatment, Wi-Fi may not be desirable. Accordingly, in some embodiments, afterloader 10 and junction box 30 may communicate via an infrared wireless network. For example, a direct line-of-sight transmission may be used to wirelessly transmit data. An infrared transceiver may be located within treatment room 100 (e.g., mounted on a ceiling, wall, ground, or other suitable structure) and may be operably connected to junction box 30. Afterloader 10 may also include an infrared transceiver. The use of infrared wireless systems may provide several benefits—for example, infrared devices generally use less power and therefore may not drain a battery associated with one or both of afterloader 10 and/or junction box 30 as much. Infrared signals may also be shorter range and therefore may not travel far outside of the immediate connection within treatment room 100. Accordingly, an infrared wireless system may be more secure and concerns about signal tampering may be reduced. Additionally, infrared systems may not be subject to radio frequency interference issues or signal conflicts, and thus may operate smoothly even if medical imaging (e.g., MRI) is being used while afterloader 10 is administering treatment.

Still other embodiments of wireless afterloader 10 may operate using light fidelity (Li-Fi) transmissions. A Li-Fi transceiver may be located within treatment room 100 (e.g., mounted on a ceiling, wall, ground, or other suitable structure) and may be operably connected to junction box 30. Afterloader 10 may also include a Li-Fi transceiver, e.g., one or more light-emitting diodes. Li-Fi embodiments may offer similar advantages as infrared embodiments, for example, Li-Fi signals may be shorter range and less susceptible to tampering and may be less susceptible to electromagnetic interference, and thus ideal for use in a hospital and/or during use of medical imaging, e.g., MRI. Other wireless embodiments of afterloader 10 may use a wireless ultrasound, Wi-Fi, Bluetooth, ZigBee, or other suitable method of wirelessly connecting.

In exemplary embodiments, wireless brachytherapy treatment system 1 may be used as follows. A subject may be prepped for brachytherapy treatment (e.g., imaging may be performed, a brachytherapy applicator may be placed, etc.), and the subject may be placed in treatment room 100. Afterloader 10 may be hooked up to the subject, e.g., by connecting one or more transfer tubes. Medical personnel may exit treatment room 100 and seal treatment room 100 to prevent radiation from escaping from treatment room 100. Medical personnel may then begin a treatment procedure by activating afterloader 10 from outside of treatment room 100. For example, the medical personnel may be located in control room 200.

Once afterloader 10 is activated, a first signal with a first value may be communicated between afterloader 10 and junction box 30. As discussed above, CPLDs 14a and 31a may communicate wirelessly approximately every 5-10 milliseconds, approximately every 5-20 milliseconds, approximately every 5-50 milliseconds, approximately every 10-20 milliseconds, approximately every 10-30 milliseconds, etc. If CPLD 14a or CPLD 31a determines that the first value is as expected, then CPLD14a or CPLD 31a may transmit a second signal with a second value. The treatment procedure may continue until the completion of the procedure, unless the first value and the second value do not correspond as expected. In some embodiments, the treatment procedure may continue until completion unless no signal is received by either CPLD 31a or CPLD 14a or a termination instruction is received by either CPLD 31a or CPLD 14a. In the event that a termination instruction is received, the first and second values do not correspond as expected, and/or a signal is not received by afterloader 10 within the time period discussed above, afterloader 10 may stop administering brachytherapy treatment. As described herein, this may include retracting sources and/or any radioactive material into a shielded compartment of afterloader 10 and sealing the compartment. Once the compartment is sealed to prevent radioactive material from escaping, afterloader 10 may be moved away from the subject, either manually (e.g., by pushing afterloader 10 or by initiating motorized control of afterloader 10) or automatically (e.g., afterloader 10 may be configured to move back to docking station 20 after the transfer tubes or any other accessories have been disconnected from the subject following brachytherapy treatment).

In some embodiments, afterloader 10 may be docked at docking station 20 prior to use during a brachytherapy treatment procedure. For example, docking station 20 may unlock afterloader 10 (if locked), and charging of afterloader 10 may be stopped, in the event that afterloader 10 is charging. After dissociation from docking station 20, afterloader 10 may be moved to a location adjacent the subject. Control of afterloader 10 may be performed wirelessly via a manual control by the medical personnel or via a predetermined program.

Once afterloader 10 is in the appropriate position, radioactive material, e.g., one or more radioactive sources, seeds, etc., may be extended therefrom. The radioactive material may be included within one or more of a capsule, a needle, a tube, a catheter, or any other device known to one of the art to move radioactive material into a subject. After completion of the brachytherapy treatment, the radioactive material may be removed from the subject.

Once the radioactive material is stored within a compartment of afterloader 10, a cover may, in some embodiments, be used to seal the compartment to prevent radiation from escaping. Afterloader 10 may be subsequently moved away from the subject. According to an exemplary embodiment, afterloader 10 may move to a location in the treatment room 100, e.g., to docking station 20. Afterloader 10 may be locked to or within docking station 20 and/or may be electrically connected to docking station 20 to charge one or more batteries associated with afterloader 10. According to exemplary embodiments, once afterloader 10 is moved to the designated location, afterloader 10 may be shut down.

As described herein, it will be understood that the treatment procedure may continue until an emergency retract protocol or a termination signal is communicated to afterloader 10 or until the treatment administration is complete. An emergency retract protocol or termination signal may include, e.g., a signal received by afterloader 10 from CPLD 31a with an unexpected value, a low battery signal or a signal that a backup battery is now being used, a signal that the treatment procedure is not operating correctly or that one or more devices of the system are not functioning correctly, and/or failure of a signal to be received by afterloader 10 from CPLD 31a within a certain amount of time. Any such emergency event may cause the treatment procedure to be terminated, as described above.

Embodiments of the wireless afterloaders described herein may provide one or more of the following benefits. Afterloaders 10 may be used interchangeably in different treatment rooms 100. For example, a common junction box 30 (and/or a single treatment control computer or treatment control panel) may be present in one location, e.g., a control room 200, which may be operably connected to a plurality of access points 39 (e.g., PoE/infrared/Li-Fi/ultrasound access points), each located within a different treatment room 100. An afterloader 10 may be used to administer treatment in any of the treatment rooms 100 interchangeably. Because afterloader 10 is wireless, afterloader 10 may be wheeled or otherwise moved to a different treatment room 100 and set up for use. No power, signal, and/or potential equalization cords may need to be connected—in some embodiments, afterloader 10 may be moved into a treatment room and be ready to use. In this way, setup of afterloader 10 may be simpler and quicker. This may decrease turnover time between brachytherapy treatments and may decrease brachytherapy treatment administration time.

Afterloader 10 may also be easier to maneuver because of the lack of cords. Further, with wired afterloaders, treatment facilities may purchase multiple cables to keep in each treatment room 100 and/or purchase backup cables to keep on hand in case a cable failed or broke. In some cases, different sizes, locations, and/or arrangements of different treatment rooms 100 at a treatment facility may require different sizes of cables in different rooms, requiring a facility to purchase and/or store extra cables of multiple different sizes, adding to overhead costs of brachytherapy treatment. With a wireless afterloader, however, this overhead may be eliminated. Further, a manufacturer of wireless afterloader 10 may not need to provide cables, or multiple lengths of cables, along with afterloader 10.

Additionally, with a wireless afterloader 10, there may be no risk of damage or failure of the cables and/or connectors that could result in current leakage, which could endanger a subject receiving treatment and/or a healthcare provider or other person in the vicinity of afterloader 10. Further, people would not have to worry about tripping over cables and/or cables hindering movement of afterloader 10. Afterloader 10 may also be easier to manufacture, because no connectors, or fewer connectors, may need to be incorporated into afterloader 10. Further, service engineers, hospital personnel, medical professionals, and/or other people may be able to execute service procedures via a wireless connection using a computer, tablet, and/or smartphone rather than a hardwired connection, allowing for faster service procedures, less costly service procedures, and/or service procedures performed from a remote location. Having a wireless connection may mean that a service provider does not need to remove any covers on afterloader 10 and/or handle afterloader 10, which may take additional time. Wireless afterloaders may also increase the mean time between failures for the reasons described above (e.g., no cord damage or damaged connectors, etc.).

Further, when wired afterloaders are used with medical imaging, e.g., MRI, the afterloader cables may create artefacts in the MR images. This may require the use of expensive shielded cables to alleviate this problem. However, wireless afterloaders 10, as described herein, may be compatible with medical imaging, like MM. This may expand usage of afterloaders and allow them to be used with technology like combined MM and linear accelerators (LINAC), such as the Unity® LINAC by Elekta.

Wireless afterloaders 10 may also increase the use of brachytherapy treatment. For example, in some regions, (e.g., in regions with unstable power supply, etc.), it may be possible to continue treatment during a power fail, e.g., in battery-powered embodiments, as described above. For example, if both junction box 30 and afterloader 10 (and/or access point 39) are battery operated and/or include battery back-ups, then CPLDs 14a, 31a may be able to communicate with each other even after loss of power, allowing treatment to continue to be administered even during a power outage.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A wireless afterloader, comprising:
    a central processing unit;
    a first complex programmable logic device having a memory;
    a transceiver operably connected to the first complex programmable logic device, wherein the transceiver is configured to wirelessly transmit and receive signals to and from a second complex programmable logic device separate from the wireless afterloader; and
    a battery;
    wherein the first complex programmable logic device is configured to:
        transmit, via the transceiver, a first signal including a first value to the second complex programmable logic device;
        receive, via the transceiver, a second signal including a second value from the second complex programmable logic device;
        determine whether the first value corresponds with the second value; and
        in response to a determination that the first value does not correspond with the second value, cause the wireless afterloader to stop administration of brachytherapy treatment.

2. The wireless afterloader of claim 1, wherein the battery is a first battery, and the wireless afterloader further comprises a second battery.

3. The wireless afterloader of claim 1, wherein the transceiver is one of a Wi-Fi transceiver, a Li-Fi transceiver, an infrared transceiver, or an ultrasound transceiver.

4. The wireless afterloader of claim 1, further comprising a wireless interface for connecting to at least one of a computer, a smart phone, or a tablet.

5. The wireless afterloader of claim 1, wherein the memory includes a lookup table stored thereon.

6. The wireless afterloader of claim 1, wherein the battery includes at least one of a lead-crystal battery, a lithium-ion battery, an ultracapacitor, a supercapacitor, or a gold capacitor.

7. The wireless afterloader of claim 1, wherein the battery is configured for wireless charging.

8. The wireless afterloader of claim 1, wherein the battery is configured for wired charging.

9. A brachytherapy treatment system comprising:
    a wireless afterloader, wherein the wireless afterloader comprises:
        a central processing unit;
        a first complex programmable logic device having a memory;
        a first transceiver operably connected to the first complex programmable logic device; and
        a battery;
    a junction box;
    a second complex programmable logic device having a memory, wherein the first complex programmable logic device is separate from the second complex programmable logic device;
    an access point operably coupled to the junction box and the second complex programmable logic device;
    a second transceiver operably coupled to the access point; and at least one emergency stop switch operably coupled to the second complex programmable logic device;

wherein the first complex programmable logic device is configured to:

transmit, via the first transceiver, a first signal including a first value to the second complex programmable logic device;

receive a second signal including a second value from the second complex programmable logic device via the first transceiver;

determine whether the first value corresponds with the second value; and in response to a determination that the first value does not correspond with the second value, cause the wireless afterloader to stop administration of brachytherapy treatment.

10. The system of claim 9, wherein the junction box is located in a first room, and the wireless afterloader is located within a second room.

11. The system of claim 9, wherein the first transceiver and the second transceiver are one of a Wi-Fi transceiver, a Li-Fi transceiver, an infrared transceiver, or an ultrasound transceiver.

12. The system of claim 9, wherein the battery includes a first battery, and the system further includes a second battery operably coupled to the junction box.

13. The system of claim 9, wherein the second complex programmable logic device is included as part of the junction box.

14. The system of claim 9, wherein the memory of the first complex programmable logic device includes a first lookup table stored thereon, and the memory of the second complex programmable logic device includes a second lookup table stored thereon.

15. The system of claim 9, further comprising a docking station configured to store and/or charge the wireless afterloader.

16. A wireless afterloader, comprising:

a complex programmable logic device having a memory with a lookup table stored thereon;

a transceiver operably connected to the complex programmable logic device, wherein the transceiver is configured to receive wireless data; and a battery;

wherein the transceiver is configured to receive a first wireless signal, and, in response to receiving the first wireless signal, the complex programmable logic device is configured to access the lookup table to determine whether a value associated with the first wireless signal corresponds to a value stored in the lookup table;

wherein, if the value associated with the first wireless signal does not correspond to the value stored in the lookup table, the wireless afterloader is configured to stop administering brachytherapy treatment.

17. The wireless afterloader of claim 16, wherein the transceiver is one of a Wi-Fi transceiver, a Li-Fi transceiver, an infrared transceiver, or an ultrasound transceiver.

18. The wireless afterloader of claim 16, wherein the battery is a first battery, and the wireless afterloader further comprises a second battery.

19. The wireless afterloader of claim 16, wherein the battery includes at least one of a lead-crystal battery, a lithium-ion battery, an ultracapacitor, a supercapacitor, or a gold capacitor.

20. The wireless afterloader of claim 16, wherein the battery is configured for wireless charging.

* * * * *